(12) United States Patent
Kim et al.

(10) Patent No.: US 6,440,565 B1
(45) Date of Patent: Aug. 27, 2002

(54) BIOCOMPATIBLE METALLIC MATERIALS GRAFTED WITH SULFONATED POLY (ETHYLENE OXIDE) AND PREPARATION THEREOF

(75) Inventors: Young-Ha Kim; Ki-Dong Park; Dong-Jun Ahn; Soo-Hyun Kim, all of Seoul; Won-Kyu Lee, Taejon, all of (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/662,865

(22) Filed: Sep. 15, 2000

(30) Foreign Application Priority Data

Jan. 11, 2000 (KR) .......................................... 2000-1095

(51) Int. Cl.[7] .............................................. B32B 27/36
(52) U.S. Cl. ................................................... 428/411.1
(58) Field of Search ...................................... 428/411.1

(56) References Cited

U.S. PATENT DOCUMENTS

| | | | |
|---|---|---|---|
| 5,824,045 A | 10/1998 | Alt ................................ | 623/1 |
| 5,843,172 A | 12/1998 | Yan | |
| 5,897,911 A | 4/1999 | Loeffler ......................... | 427/2 |
| 5,919,126 A | 7/1999 | Armini | |
| 5,976,169 A | 11/1999 | Imran | |

OTHER PUBLICATIONS

Won Kyu Lee, et al. "Self–Assembled Monolayers of Sulfonated Poly(ethylene oxide) on Gold Surfaces". Transactions vol. 4, No. 2. '99 Fall Meeting of the Korean Society for Biomaterials (Korea–Japan Joint Symposium on Biomaterials) pp. 179–180.

P. Harder, et al., J. Phys. Chem. B, vol. 102, No. 2, pp. 426–436, "Molecular Conformation in Oligo(Ethylene Glycol)–Terminated Self–Assembled Monolayers on Gold and Silver Surfaces Determines Their Ability to Resist Protein Adsorption", 1998.

Frits W. Baer, et al., 2000 John Wiley & Sons, Inc., pp. 193–198, "New Biocompatible Polymer Surface Coating for Stents Results in a low Neointimal Response", 1999.

Abraham Ulman, Chemical Reviews, vol. 96, No. 4, pp. 1533–1554, "Formation and Structure of Self–Assembled Monolayers", 1996.

*Primary Examiner*—Terressa M. Boykin
(74) *Attorney, Agent, or Firm*—Oblon, Spivak, McClelland, Maier & Neustadt, P.C.

(57) ABSTRACT

A surface-modified medical metallic material, which comprise a metallic substrate; a thin film of gold or silver coated on the surface of said substrate; a functional sulfur compound adsorbed on said thin film; and a sulfonated poly (ethylene oxide) (PEO) derivative chemically bonded to functional groups of said sulfur compound, and a method for the preparation thereof are disclosed. It is also disclosed a stent, a cardiac valve and a catheter prepared from the surface-modified metal material.

19 Claims, No Drawings

BIOCOMPATIBLE METALLIC MATERIALS GRAFTED WITH SULFONATED POLY (ETHYLENE OXIDE) AND PREPARATION THEREOF

BACKGROUND OF THE INVENTION

1. Field of the Invention

The present invention relates to surface-modified metallic materials for medical purposes, in particular materials for use in circulatory medical devices. More specifically, the present invention relates to surface-modified metallic materials prepared by coating a thin film of gold or silver on the surface of metallic substrates, attaching to said thin film functional sulfur compounds having high adsorptivity, and chemically bonding sulfonated poly(ethylene oxide) (PEO) (alternatively, referred to as poly(ethylene) glycol, PEG) to functional groups of said sulfur compounds. The materials of the invention have remarkably improved antithrombogenicity and biocompatibility and thus are especially useful for medical devices such as prosthetic cardiac valves, stents and catheters.

2. Description of the Prior Art

Prosthetic cardiac valves have been implanted and used as substitutes for cardiac valves that have been impaired through hereditary or acquired means. Examples of prosthetic cardiac valves include valves made from tissues and mechanical valves made from metallic materials such as titanium. The tissue valves have good biocompatibility but have a drawback in that their internal durability is inferior due to calcification. The mechanical valves have excellent durability but are defective in that they may be accompanied by the formation of thrombus, requiring the patient to take anticoagulants throughout his or her life. Intensive research has been conducted in the art in order to improve the antithrombogenicity of mechanical valves. But because the formation of thrombus is a normal physiological phenomenon, it is impossible to completely prevent it. Moreover, the formation mechanism of thrombus has not yet been completely explained.

In order to treat the stricture of the coronary arteries, a percutaneous transluminal coronary angioplasty in which blood vessels are expanded by inserting intraaortic baloon catheters into the coronary arteries has been commonly used. This angioplasty has produced relatively good results, and its operation method and apparatus have been continuously developed. However, problems such as chronic closure and restenosis are still unsolved.

Stents are metallic implants in the form of a spring which are inserted into blood vessels to keep them expanded after the angioplasty has been carried out in order to prevent restenosis. Recently, the use of stents has increased. Stents are made from stainless steel, tantalum or titanium-nickel alloys and the like, and various types of stents, such as balloons or tubes have been developed and used. However, it has been found that the effort to prevent restenosis meets with failure about 20% to 30% of the time, even in cases when stents are implanted. It has been also ascertained that the main cause of such failure are restenosis, which is caused by an acute and chronic thrombus formation and the proliferation of smooth muscle cells in the internal walls of blood vessels from the wounds inflicted when inserting stents. The inherent properties of metals make it easy for thrombus to easily form on the surface thereof. Metal surfaces generally have a positive charge and, thus, exhibit high interreactivity with blood having a negative charge. Also, it has been ascertained that metals have high critical surface tension and thus are easily susceptible to the formation of thrombus, as noted by M.F.A. Goosen, et al. in Biomaterials, 17, 685–694 (1996).

U.S. Pat. No. 5,824,045, granted to E. Alt, and U.S. Pat. No. 5,976,169, granted to M. A. Imran, disclose attempts to improve the antithrombogenicity and to reduce allergic reactions of stents made from stainless steel and the like, by vapor deposition of a thin film of gold, platinum, silver or an alloy thereof on the surface of stents. However, these attempts have failed to provide a superior antithrombogenicity effect.

Also, U.S. Pat. No. 5,919,126 granted to A. J. Annini, discloses stents for the prevention of the restenosis by beta-ray emission, which are prepared by vapor deposition of a thin film of gold, platinum, titanium, nickel or the like on the surface thereof made from stainless steel, titanium or nickel-titanium alloy, and then by implanting radioisotopes to the film.

Further, many studies have been made in the art wherein polymers are coated on the surface of metallic materials which are to be used in the preparation of mechanical valves and stents in order to improve their antithromgenicity. For example, a method comprising the covering of the metallic surface with nylon mesh (See T. Yoshioka, et al., Am. J. Radiol., 15, 673–676, 1988), or a method comprising the coating of the metallic surface with silicone (See T. Roeren, et al., Radiology 174, 1069, 1990) or polyurethane (See I. K. De Scheerder, et al., J. Am. Coll. Cardiol 23, 186A, 1994) have been proposed, but these methods have not produced satisfactory results.

Further, there are proposed methods comprising the coating of the metallic surface with polymers having grafted heparin as an anticoagulant (See S. Stheth, et al., J. Am. Coll. Cardiol 23, 187A, 1994), with fibrin (See R. S. Schwartz, et al., J. Am. Coll. Cardiol 19, 171A, 1992), or with polymers containing agents such as dexamethasone (See A. M. Lincoff, et al., J. Am. Coll. Cardiol 23, 18A, 1994) such that the agents can be released slowly. However, these methods also failed to obtain the desired results.

In order to enhance the antithromgenicity of metallic materials for medical uses, many studies have been made with respect to anionic surfaces or structures having hydrophilic, hydrophobic and hydrophilic/hydrophobic micro-domains. It has been reported that a PEO-grafted surface prevents the adhesion of blood components such as proteins and blood platelets thereto and thus improves the antithromgenicity thereof (See J. D. Andrade, et al., Biomaterials 11, 455, 1990). It has also been reported that the PEO-grafted surface largely reduces the adhesion and spreading of cells as well as the adhesion and infection of bacteria (See J. A. Hubbell, et al., Biomaterials 13, 417, 1992).

Because metals have no functional groups that are chemically active, unlike polymers, i.e., organic materials, it is impossible to chemically modify them. There are some examples where PEO, poly(vinyl alcohol) or similar hydrophilic polymers have been applied to the surface of metals, especially stents, in order to modify the surface (See U.S. Pat. No. 5,843,172, granted to J. Y. Yan and U.S. Pat. No. 5,897,911, granted to J. P. Loeffler). However, because the polymers were simply coated on the metal surface, adhesive strength is poor and the antithromgenicity is below the desired level.

M. Grunze, et al. studied and reported that in a PEO self-assembled monolayer wherein the PEO is grafted to the surface of gold or silver film by means of sulfur compounds, the adsorption of protein is reduced (See J. Phys. Chem. B, 102, 426–436, 1998). Similar studies are in progress. However, it is impossible to obtain a practically applicable level of antithromgenicity, and there have been no reports on its commercialization.

We, the present inventors, found that the grafting of sulfonated poly(ethylene oxide) to the surface of polymers adds antithrombotic effects of the sulfonate group to the non-adhesion property of the PEO, thereby highly enhancing the antithrombogenicity and biocompatibility of the surface of the polymers (See Korean Patent. No. 62,921 to Y. H. Kim et al.).

The present inventors have now found that excellent antithrombogenicity and biocompatibility of metals can be obtained by chemically binding sulfonated PEO through sulfur compounds to thin film of gold or silver that is then stably coated on the surface of the metals. In other words, the present inventors have solved the problems mentioned above by discovering a thin film of gold or silver that could be stably coated on a metallic surface; sulfur compounds that form charge transfer complexes with said thin films and are strongly adsorbed onto the films; and sulfonated PEO derivatives that chemically bond to said sulfur compounds.

SUMMARY OF THE INVENTION

Thus, the object of the present invention is to provide metallic materials for medical purposes with remarkably improved antithrombogenicity and biocompatibility which are prepared by coating a thin film of gold or silver on a metallic surface by electroplating, vacuum vapor deposition, or ion sputtering methods, attaching thereto a sulfur compound having strong adsorptivity to said thin film, and then chemically bonding a sulfonated PEO derivative to functional groups of said adsorbed sulfur compound, and to provide a method for preparing the metallic materials.

The further object of the present invention is to provide circulatory medical devices, in particular, stents, prosthetic cardiac valves and catheters by using metallic materials that reduce the thrombogenicity and the adhesion and interaction of proteins and cells as a result of the synergic effects of the combination of the antithrombogenicity of sulfonic acid and the non-adhesion property of PEO.

DETAILED DESCRIPTION OF THE INVENTION

The medical metallic materials according to the invention comprise
- a metallic substrate;
- a thin film of gold or silver coated on the surface of said substrate;
- a functional sulfur compound adsorbed on said film; and
- a sulfonated poly(ethylene oxide) (PEO) derivative chemically bonded to functional groups of said sulfur compound.

Metals which can be used as metallic substrates include, without limitation, iron, stainless steel, nickel, chromium, copper, titanium, tantalum and alloys thereof. A thin film of gold or silver generally has a thickness of tens of micrometers, but possibly up to several hundred micrometers. The thin film of gold or silver of the inventive metallic materials typically have a thickness of 0.1 to 100 μm; whereas the ultrathin film of chromium, titanium or an alloy thereof having a thickness of about 0.01 to 1 μm can be inserted between the surface of the metallic substrate and the thin film of gold or silver (See U.S. Pat. No. 5,919,126 to A. J. Armini).

A functional sulfur compound is formed as a self-assembled monolayer by chemisorption on the surface of a thin film of gold or silver (analyses have shown that said sulfur compound forms a charge transfer complex). Said functional sulfur compound is prepared by bonding functional groups such as hydroxyl, amino, isocyanate, aldehyde, carboxyl or its acid chloride, acid anhydride or acid amide, succinimidyl ester, succinimidyl carbonate, tresilyl, oxycarbonyl imidazole or nitrophenyl carbonate group to alkanethiol, dialkylsulfide, dialkyldisulfide, alkylxanthate, dialkylthiocarbamate.

More specifically, functional sulfur compounds, which can be used in the present invention, are those represented by the general formulas (1) to (5) that are given below. The compounds of general formula (4) or (5) may be also used in the form of salt or ester thereof:

$$Y—R—SH \quad (1)$$
$$Y—R—S—R'—Y \quad (2)$$
$$Y—R—S—S—R'—Y \quad (3)$$
$$Y—R—O—CSSH \quad (4)$$
$$(Y—R)_2—N—CSSH \quad (5)$$

wherein
Y is hydroxyl, amino, isocyanate, aldehyde, carboxyl or its acid chloride, acid anhydride or acid amide, succinimidyl ester, succinimidyl carbonate, tresilyl, oxycarbonyl imidazole or nitrophenyl carbonate; and
R and R' are independently $C_2$–$C_{25}$ alkyl.

Examples of the alkanethiols-functional sulfur compound represented by the general formula 1 include, without limitation, mercaptoethanol, mercaptopropanol, mercaptobutanol, aminoethanethiol, aminomethylpropanethiol, mercaptoacetic acid, mercaptopropionic acid, mercaptosuccinic acid, thiolactic acid and substituted derivatives thereof.

Examples of the dialkylsulfides-functional sulfur compound represented by the general formula 2 include, without limitation, thiodiethanol, thiodipropanol, methylthioethanol, methylthiopropanol, methylthiobutanol, ethylhydroxyethyl sulfide, glucose dimethyl mercaptal, thioethylethyl amine, thiodiglycolic acid, thiodipropionic acid, methylthioacetic acid and substituted derivatives thereof.

Examples of the dialkyldisulfides-functional sulfur compound represented by the general formula 3 include, without limitation, hydroxyethyl disulfide, cystamine, dithiodipropionic acid, dithiodibutyric acid and substituted derivatives thereof.

Functional sulfur compounds, thus adsorbed on the metallic surface of a thin film of gold or silver, have a very strong bonding force that makes them stable under any kind of friction or various chemical environment such as weak acid or alkali, non-concentrated solvent, etc. Thus, they do not present any risks when applied to the human body or in other medical uses.

The sulfonated PEO derivatives should have a sulfonic acid group on one end and a functional group (X) which can be bonded to a functional group (Y) of sulfur compounds on the other end. Thus, their structure can be represented by the general formula 6 below:

$$HO_3S—A—PEO—B—X \quad (6)$$

wherein
PEO is a poly(ethylene oxide) residue represented by the formula —$(CH_2—CH_2—O)_n$—, wherein n is a integer from 5 to 250;

A and B are the same or different, and represents a $C_1$–$C_3$ alkylene group; and X is selected from the group consisting of hydroxyl, amino, carboxyl, epoxy, aldehyde, succinimidyl ester, succinimidyl carbonate, tresilyl, oxycarbonyl imidazole and nitrophenyl carbonate group.

The molecular weight of a PEO unit of sulfonated PEO derivatives is from 200 to 15,000, more preferably from 500 to 10,000. If the molecular weight of PEO is smaller than 500, then the biological function of PEO, i.e., the function to reduce the adhesion of proteins, bloods and cells, is too small to have any effect. Because said function does not increase proportional to the molecular weight, the molecular weight of PEO over 10,000 is unnecessary.

The present invention is also related to a method for the production of a surface-modified medical metallic material, which comprises the steps of:

(a) providing a metallic substrate;

(b) coating a thin film of gold or silver on the surface of said substrate;

(c) applying on said film a functional sulfur compound which can form a charge transfer complex with said film, thereby be adsorbed on said film; and (d) chemically bonding a sulfonated poly(ethylene oxide) (PEO) derivative to the functional groups of said sulfur compound.

Metals which can be used as metallic substrate include, without limitation, iron, stainless steel, nickel, chromium, copper, titanium, tantalum and alloys thereof.

The coating method in step (b) includes the electroplating, chemical vapor deposition, ion sputtering and thermal vapor deposition method.

The electroplating method is a method wherein a gold or silver coat is plated by using a gold or silver cyanide plating solution and applying a voltage of about 6 volts, and it has the advantage of a uniformly plated coat even though the shape of the substrate is complex. The thermal vapor deposition method is a method wherein thin film materials are deposited under a supervacuum state of $10^{-8}$ mmHg at high temperature, close to their melting point. The ion sputtering method is also a method wherein thin film materials are ionized deposited by a current energy under a supervacuum state. An example of this method is the vacuum deposition of a thin film of gold, silver, aluminum or the like, which is well known in the art. But such method has disadvantages that it is difficult to uniformly deposit a substrate having a complex shape. The chemical vapor deposition method is characterized by the decomposition of thin film materials on the surface of a substrate to form the thin film. Although such method is carried out at ambient temperature and low pressure, it is not suitable in the present invention.

Generally, a thin film has a thickness of tens of micrometers or lower, but possibly up to several hundred micrometers. According to the present invention, the thin film of gold or silver is formed to a thickness of 0.1 to 100 $\mu$m. Generally, stable thin films having abrasion resistance are formed, although they are somewhat different in term of roughness, stability and abrasion resistance, depending on the method used.

According to a preferred embodiment of the present invention, an ultrathin film of chromium, titanium or an alloy thereof can be deposited in a thickness of 0.1 to 0.5 $\mu$m prior to step (b) to enhance the adhesion between a metal and a thin film of gold or silver.

In the adsorption of the functional sulfur compound in step (c), a functional sulfur compound is chemically adsorbed on the surface to self-assembled monolayer film (analyses have shown that said sulfur compound forms a charge transfer complex). Functional sulfur compounds useful for the adsorption in step (c) include those prepared by bonding a functional group (Y) to alkanethiol, dialkylsulfide, dialkyldifulfide, alkylxanthate and dialkylthiocarbamate, as described above. The above functional group (Y) is that which can be reacted with the functinal group (X) of the sulfonated PEO derivatives to be bonded in step (d). Group (Y) is selected from the group consisting of hydroxyl, amino, isocyanate, aldehyde, carboxyl or its acid chloride, acid anhydride or acid amide, succinimidyl ester, succinimidyl carbonate, tresilyl, oxycarbonyl imidazole or nitrophenyl carbonate group.

More specifically, functional sulfur compounds useful for the present invention include alkanethiols, such as mercaptoethanol, mercaptopropanol, mercaptobutanol, aminoethanethiol, aminomethylpropanethiol, mercaptoacetic acid, mercaptopropionic acid, mercaptosuccinic acid, thiolactic acid; dialkylsulfides, such as thiodiethanol, thiodipropanol, methylthioethanol, methylthiopropanol, methylthiobutanol, ethylhydroxyethyl sulfide, glucose dimethyl mercaptal, thioethylethyl amine, thiodiglycolic acid, thiodipropionic acid, methylthioacetic acid; dialkyldisulfides, such as hydroxyethyl disulfide, cystamine, dithiodipropionic acid, dithiodibutyric acid, etc. These sulfur compounds can be introduced with said other functional groups by means of a suitable substitution reaction. Alkyxthanates- and dialkylthiocarbamates-sulfur compounds, including suitable functional group (Y), are rarely available commercially as derivatives, but can be prepared by a known method in the art from the corresponding starting materials.

It has been reported that such functional sulfur compounds, in general, more easily and stably adhere to the surface of gold than that of silver (See A. Ulman, Chem. Rev. 96, 1533–1554, 1996).

The adsorption process of functional sulfur compounds is carried out by preparing the above functional sulfur compound as a diluted solution, and immersing a metal sample therein at ambient temperature for 6 to 24 hours. Alcohol is used as a solvent for sulfur compound, and the solution is used at a concentration of from 0.5 mMol to 2 mMol, preferably 1 mMol.

The sulfonated PEO derivatives used in step (d) should have a sulfonic acid group on one end and a functional group (X) which can be bonded with a functional group (Y) of sulfur compounds on the other end as described above.

More specifically, the sulfonated PEO derivatives useful in the present invention can be prepared by reacting usual PEO having hydroxyl group at both ends or by reacting PEO derivatives that are substituted by amino, carboxyl, epoxy, aldehyde, succinimidyl ester or the like at both ends with propane sultone or with a compound containing both sulfonic acid group and amino or other functional groups, for example, taurine (aminoethylsulfonic acid) or the like (See M. Harris, et al., PEO Chemistry and Biological Applications, ACS, 1997), which is shown but not limited to Schemes 1 to 6 below. Said PEO derivatives are commercially available from Shearwater (U.S.A.) or Nippon Oil Industrial Co., Ltd. (Japan):

Scheme 1

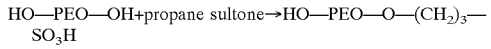

Scheme 2

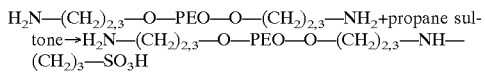

Scheme 3

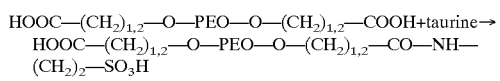

Scheme 4

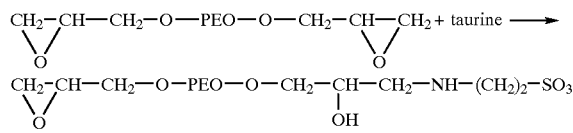

Scheme 5

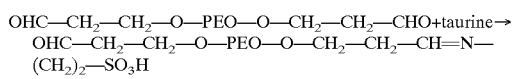

Scheme 6

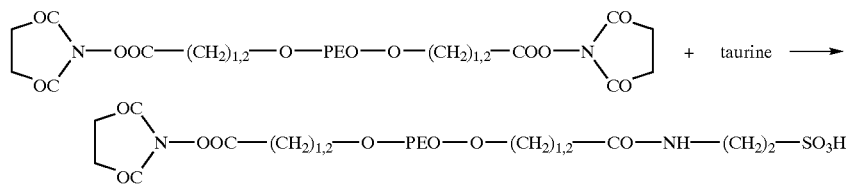

wherein,
$(CH_2)_{2,3}$ and $(CH_2)_{1,2}$ represent those having 2 or 3, and 1 or 2 of $CH_2$ groups, respectively.

A functional sulfur compound that can be adsorbed on a thin film of gold or silver, and sulfonated PEO derivatives bonded thereto are in principle indefinite in the selection. Thus, they are commercially available or can be prepared from the available compounds by methods known in the art. An economically feasable method should be found whereby starting materials can be made easily available to reduce costs and enable one to conveniently and simply carry out this process. That is, the reaction scheme should be designed, as in scheme 7 below, such that the sulfonated PEO derivatives have a sulfonic acid on one end and a functional group (X), which can be bonded to a sulfur compound at other end, and that the sulfur compounds contain a functional group (Y) which can be bonded with said functional group (X).

Scheme 7

HO$_3$S—A—PEO—B—X+Y—R-Sulfur Compound/Thin film of gold or silver/Metal→HO$_3$S—A—PEO—B—X—Y—R-Sulfur Compound/Thin film of gold or silver/Metal The functional group (Y) of sulfur compounds that can be bonded with the functional group (X) of sulfonated PEO derivatives is summarized in Table 1 below.

TABLE 1

| Functional group (X) of the sulfonated PEO derivatives | Functional group (Y) of the sulfur compounds |
|---|---|
| -hydroxyl group | -carboxyl group and acid chloride, acid anhydride, acid amide group as derivatives |

TABLE 1-continued

| Functional group (X) of the sulfonated PEO derivatives | Functional group (Y) of the sulfur compounds |
|---|---|
| | -isocyanate group, -aldehyde group, -succinimidylester group, succinimidyl carbonate group, tresilyl group, oxycarbonyl imidazole group, nitrophenyl carbonate group |
| -amino group | -carboxyl group and acid chloride, acid anhydride, acid amide group as derivatives -isocyanate group, -aldehyde group, -epoxy group -succinimidylester group, succinimidyl carbonate group, tresilyl group, oxycarbonyl imidazole group, nitrophenyl carbonate group |
| -carboxyl group | -amino group, -acid chloride, acid anhydride, acid amide |

TABLE 1-continued

| Functional group (X) of the sulfonated PEO derivatives | Functional group (Y) of the sulfur compounds |
|---|---|
| | group, -isocyanate group, -epoxy group |
| -epoxy group | -amino group, -carboxyl group |
| -aldehyde group | -amino group, -hydroxyl group |
| -succinimidyl ester group, succinimidyl carbonate group, tresilyl group, oxycarbonyl imidazole group, nitrophenyl carbonate group | -hydroxyl group, -amino group |

The binding reactions of the sulfur compounds and the sulfonated PEO derivatives according to the above Scheme 7 proceed as in Schemes 8 and 9, and various methods are possible depending on the types of X and Y and the types of sulfur compounds.

Scheme 8

HOOC—R—S—S—R'—COOH or
            HOOC—R—S—R'—COOH +

H$_2$N—(CH$_2$)$_{2,3}$—O—PEO—O—(CH$_2$)$_{2,3}$—NH—(CH$_2$)$_3$—SO$_3$H →

S—R—CO—NH—A—O—PEO—O—(CH$_2$)$_{2,3}$—NH—A—SO$_3$H
|
S—R'—CO—NH—A—O—PEO—O—(CH$_2$)$_{2,3}$—NH—A—SO$_3$H   or

-continued

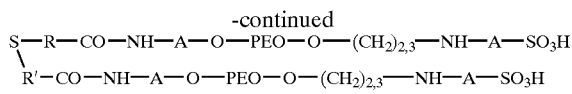

DESCRIPTION OF THE PREFERRED EMBODIMENTS

The present invention will be further described by the follow examples, but should not be construed as being limited by them. In the examples, the process for forming a thin film of gold or silver on the metallic substrate is performed according to the following thin film process.

Scheme 9

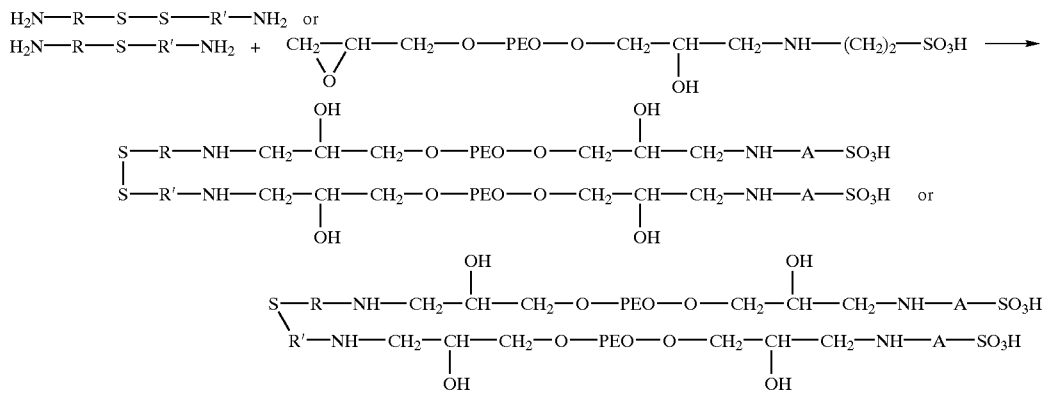

Upon binding the functional group (Y) of the sulfur compounds and the functional group (X) of the sulfonated PEO derivatives, the appropriate catalysts, i.e., the substitution and the addition catalysts such as the esterification catalysts, the amidation catalysts and the like, may be used in order to allow the binding of two compounds proceed more quantitatively.

The binding reactions between the functional group (Y) of the sulfur compound and the functional group (X) of the sulfonated PEO derivatives are carried out in aqueous solutions, more preferably in buffer solutions, except in specific cases. The reactions are performed by adjustments to the acidic or basic pH depending on the nature of each reaction.

In order to estimate the hydrophilicity of the surface as properties of the modified metal, a contact angle was determined (Model CA-DT 11931, Kyowa Interface Sci., Japan). Antithrombogenicity was estimated according to the "Measurement of Platelet Adhesion" as described below. Samples of the surface-modified metal were charged into a disposable syringe and 2 ml of a phosphate buffer solution were added. The phosphate buffer solution was replaced with 2 ml of the human platelet rich plasma ($52 \times 10^4$ of platelet/ul), the syringe was suspended in a shaking incubator controlled at 37° C. and was kept at the same temperature for a certain amount of time. The syringe was recovered, and the number of the non-adhesive platelets in the plasma was measured by a Coulter counter or Cytometer, thereby reverse-counting the number of the adhered platelets (See Hee-Jung Lee, et al., Polymer (Korea), 21, 1045–1052, 1997).

The chemical conformation of the surface was analyzed by means of ATR FTIR (Attenuated Total Reflectance Fourier Transform Infrared) and ESCA (Electron Spectroscopy for Chemical Analysis). The ATR FTIR was performed with a Bruker FTIR Apparatus (IFS 66; Bruker, German) using KRS-5 crystals. The ESCA was performed on ESCA 280-S (SSI, USA) with AlK a X-ray, with reference to the binding energy of Cls absorption area of the C—H group as 285.0 eV, by using 2.50, 1.68, 1.80 and 8.5 as collecting factor of $O_{1s}$, $N_{1s}$, $S_2P_3$ and $Na_{1s}$, and counting the ratios of O/C, N/C, S/C and Na/C. The morphology of the metal surface was analyzed by using an AFM (Atomic Force Microscope; Park Scientific Instruments, USA).

Thin Film Process

1. Thermal Vapor Deposition Process

The metal samples (1×1 cm and 1×3 cm) washed with a saturated solution of chromic acid (Aldrich, USA) were mounted on the thermal vapor deposition apparatus (Model RH900, MDC, USA). The distance between the boat-shape thin film material evaporator made of molybdenum and the samples was maintained at 20 cm, the evaporator temperature was adjusted to about 1200° C., and the vapor deposition using chromium or titanium was conducted under vacuum of about $1 \times 10^{-8}$ torr for 1 hour. The thickness of the resulting chromium or titanium ultrathin films was 200 Å. Gold or silver was then deposited for 3 hours forming a thin film of gold or silver to a thickness of about 0.2 µm.

2. Ion Sputtering Process

The metal samples (1×1 cm and 1×3 cm) washed with a saturated solution of chromic acid (Aldrich, USA) were mounted on the ion sputter (Model IB-3; Eiko Corporation, Japan). Under a vacuum of $1 \times 10^{-6}$ torr, the ionic current was adjusted to 7 mA and a chromium or titanium was then deposited for 40 minutes coating a chromium or titanium ultrathin films to a thickness of 200 Å. Consequently, gold or silver was deposited for 1 hour forming a thin film of gold or silver to a thickness of about 0.2 µm.

3. Electroplating Process

The metal samples (1×1 cm and 1×3 cm sizes), washed with a saturated solution of chromic acid (Aldrich, USA), were placed on the cathode of the electrolytic bath containing 500 ml of a solution comprising 15 g/l of gold cyanide or silver cyanide (Aldrich, USA), 100 g/l of potassium cyanide and 0.01 g/l of carbon disulfide. The platinum samples were then mounted on the anode. A current of 6 volts was applied and an ultrathin film of gold or silver was plated for 2 minutes to a thickness of 2 µm.

EXAMPLE 1

The stainless steel 316 samples (1×1 cm and 1×3 cm sizes, Korean Special Steel Co., Ltd.), which have been coated with a thin film of gold or silver or, in some cases, with an ultrathin film of chromium and a thin film of gold or silver, in accordance with said Thin Film Process, were dipped into 15 ml of 1 mM ethanol solution of 4,4'-dithiobutyric acid (Aldrich, USA) for 12 hours. The samples were removed, thoroughly washed with distilled water and dried. They were then added to 15 ml of an aqueous amino-PEO sulfonic acid solution (concentration of 5% w/v) containing 15 mg of carbodiimide (Aldrich, USA) and reacted for 24 hours. Said amino-PEO sulfonic acid was prepared by reacting 58.56 g of diamino-PEO (molecular weight of PEO: 1,000, Nippon Oil Industrial Co., Ltd., Japan) with 7.3 g of propane sultone (Aldrich, USA) in 540 ml of tetrahydrofuran to form precipitates, which were then filtered and dried (See Ki-Dong Park, et al., Biomaterials, 18, 47–51, 1997).

The results of the ESCA show that 66.8% carbon, 23.7% oxygen and 9.5% sulfur was present on the surface adsorbed with dithiobutyric acid, and that 63.5% carbon, 31.1% oxygen and 5.4% sulfur was present on the surface grafted with PEO derivatives. Thereby, it is ascertained that the reactions proceeded as desired.

The contact angle of the treated stainless steel samples was determined as being in a complete wetting state, which shows that, compared to the 56.3° of the untreated samples they were considerably hydrophilized.

The platelet adhesion rates were such that, 60 minutes after the platelet adhesion test starts, the number of the platelets adhering to the surface of the treated stainless steel decreased by about 60% when compared to the number that adhered to the surface of the untreated stainless steel, exhibiting a superior antithrombogenicity.

EXAMPLE 2

The tantalum samples (1×1 cm and 1×3 cm sizes, Aldrich, USA), which have been coated with a thin film of gold or silver or, as desired, with an ultrathin film of chromium and a thin film of gold or silver, in accordance with said Thin Film Process, were dipped into 15 ml of 1 mM ethanol solution of 3,3'-thiodipropionic acid (Aldrich, USA) for 12 hours. The sampels were removed, thoroughly washed with distilled water and dried. The resulting samples were treated in 15 ml of 1 mM benzene solution of thionyl chloride (Aldrich, USA) for 12 hours. The absorbed carboxyl group of thiodipropionic acid was replaced with acid chloride group. They were then added to 15 ml of chloroform solution (concentration 5% w/v) of amino-PEO sulfonic acid, which prepared as described in Example 1, and reacted for 24 hours.

The results of the ESCA show, as in Example 1, that carbon was present on the surface adsorbed with thiodipropionic acid, and that oxygen increased on the surface grafted with PEO derivatives. Thereby, it is ascertained that the reactions proceeded as desired.

The contact angle of the treated tantalum samples was determined as being in a complete wetting state, which shows that, compared to the 48.5° of the untreated samples they were considerably hydrophilized. The platelet adhesion rates were such that, 60 minutes after starting the platelet adhesion test, the number of the platelets adhering to the surface of the treated tantalum decreased by about 55% when compared to the number that adhered to the surface of the untreated tantalum, exhibiting a superior antithrombogenicity.

EXAMPLE 3

The nickel-titanium alloy samples (nickel 54%, titanium 46%; 1×1 cm and 1×3 cm sizes, NiTi Development Co., USA), which have been coated with a thin film of gold or silver or, as desired, with titanium ultrathin films and a thin film of gold or silver, in accordance with said Thin Film Process, were dipped into 15 ml of 1 mM ethanol solution of cystamine dihydrochloride (Aldrich, USA) for 12 hours. The samples were removed, thoroughly washed with distilled water and dried. Samples were then added to 15 ml of aqueous epoxy-PEO sulfonic acid solution (concentration of 5% w/v) and reacted for 24 hours. Said epoxy-PEO sulfonic acid was prepared by reacting 50 g of diepoxy-PEO (molecular weight of PEO: 5,000, Shearwater Polymers, USA) with 1.25 g of taurine (Dong-a Pharmaceuticals, Korea) in 500 ml of tetrahydrofuran to form precipitates, which were then filtered and dried.

The results of the ESCA show, as in Example 1, that carbon was present on the surface adsorbed with cystamine, and that oxygen increased on the surface grafted with PEO derivatives. Thereby, it is ascertained that the reactions proceeded as desired.

The contact angle of the treated nickel-titanium samples was determined as being in a complete wetting state, which shows that, compared to the 68.3° of the untreated samples they were considerably hydrophilized. The platelet adhesion rates were such that, 60 minutes after starting the platelet adhesion test, the number of the platelets adhering to the surface of the treated nickel-titanium decreased by about 58% when compared to the number that adhered to the surface of the untreated nickel-titanium, exhibiting a superior antithrombogenicity.

EXAMPLE 4

The nickel-titanium alloy samples (nickel 54%, titanium 46%; 1×1 cm and 1×3 cm sizes, NiTi Development Co., USA), which have been coated with a thin film of gold or silver or, as desired, with titanium ultrathin films and a thin film of gold or silver, in accordance with said Thin Film Process, were dipped into 15 ml of 1 mM ethanol solution of aminoethanthiol hydrochloride (Aldrich, USA) for 12 hours. The samples were removed, thoroughly washed with distilled water and dried. Samples were then added to 15 ml of aqueous oxycarbonyl imidazole-PEO sulfonic acid solution (concentration of 5% w/v) and reacted for 24 hours. Said oxycarbonyl imidazole-PEO sulfonic acid was prepared by reacting 15.3 g of dioxycarbonyl imidazole-PEO (molecular weight of PEO: 1,000; Shearwater Polymers, USA) with 1.25 g of taurine (Dong-a Pharmaceuticals, Korea) in 100 ml of tetrahydrofuran to form precipitates, which were then filtered and dried.

The results of the ESCA show, as in Example 1, that carbon was present on the surface adsorbed with aminoethanthiol, and that oxygen increased on the surface grafted with PEO derivatives. Thereby, it is ascertained that the reactions proceeded as desired.

The contact angle of the treated nickel-titanium samples was determined as being 17.5°, which shows that, compared to the 68.3° of the untreated samples they were considerably hydrophilized. The platelet adhesion rates were such that, 60 minutes after starting the platelet adhesion test, the number of the platelets adhering to the surface of the treated nickel-titanium decreased by 55% when compared to the number that adhered to the surface of the untreated nickel-titanium, exhibiting a superior antithrombogenicity.

EXAMPLE 5

The stainless steel 316 samples (1×1 cm and 1×3 cm sizes, Aldrich, USA), which have been coated with a thin film of gold or silver or, as desired, with an ultrathin film of chromium and a thin film of gold or silver, in accordance with said Thin Film process, were dipped into 15 ml of 1 mM ethanol solution of cystamine dihydrochloride (Aldrich, USA) for 12 hours. The samples were removed, thoroughly washed with distilled water and dried. Samples were then added to 15 ml of aqueous aldehydo-PEO sulfonic acid solution (concentration of 5% w/v) and reacted for 24 hours. Said aldehydo-PEO sulfonic acid was prepared by reacting 11.3 g of dialdehydo-PEO (molecular weight of PEO: 1,000; Shearwater Polymers, USA) with 1.25 g of taurine (Dong-a Pharmaceuticals, Korea) in 100 ml of tetrahydrofuran to form precipitates, which were then filtered and dried.

The results of the ESCA show, as in Example 1, that carbon was identified on the surface adsorbed with cystarnine, and that oxygen increased on the surface grafted with PEO derivatives. Thereby, it is ascertained that the reactions proceeded as desired.

The contact angle of the treated stainless steel samples was determined as being 15.6°, which shows that, compared to the 56.3° of the untreated samples they were considerably hydrophilized. The platelet adhesion rates were such that, 60 minutes after starting the platelet adhesion test, the number of platelets adhering to the surface of the treated stainless steel decreased by about 58% when compared to the number that adhered to the surface of the untreated stainless steel, exhibiting a superior antithrombogenicity.

The metallic materials, which have been plated with a thin film of gold or silver, grafted with sulfur compounds and then introduced with the sulfonated PEO derivatives according to the present invention, have an improved antithrombogenicity and biocompatibility. Thus, they are useful as metallic materials for implants such as stents, prosthetic cardiac valves and catheters.

What is claimed is:

1. A surface-modified medical metallic material, which comprises:
    a metallic substrate;
    a thin film of gold or silver coated on the surface of said substrate;
    a functional sulfur compound that forms a charge transfer complex with said film, thereby being adsorbed on said film; and
    a sulfonated poly(ethylene oxide) (PEO) derivative chemically bonded to functional groups of said sulfur compound.

2. The material according to claim 1 wherein said sulfonated PEO derivative is represented by the general formula (6) below:

HO$_3$S—A—PEO—B—X     (6)

wherein
    PEO is a poly(ethylene oxide) residue represented by the formula —(CH$_2$—CH$_2$—O)$_n$—, wherein n is a integer from 5 to 250;
    A and B are the same or different, and represents a C$_1$–C$_3$ alkylene group; and
    X is selected from the group consisting of hydroxyl, amino, carboxyl, epoxy, aldehyde, succinimidyl ester, succinimidyl carbonate, tresilyl, oxycarbonyl imidazole and nitrophenyl carbonate group.

3. The material according to claim 1 wherein said sulfur compound is represented by the general formula (1) below:

Y—R—SH     (1)

wherein
    Y is selected from the group consisting of hydroxyl, amino, isocyanate, aldehyde, carboxyl or its acid chloride, acid anhydride or acid amide, succinimidyl ester, succinimidyl carbonate, tresilyl, oxycarbonyl imidazole and nitrophenyl carbonate; and
    R represents C$_2$–C$_{25}$ alkyl.

4. The material according to claim 3 wherein said sulfur compound of the formula (1) is one selected from the group consisting of mercaptoethanol, mercaptopropanol, mercaptobutanol, aminoethanethiol, aminomethylpropanethiol, mercaptoacetic acid, mercaptopropionic acid, mercaptosuccinic acid, and thiolactic acid.

5. The material according to claim 1 wherein said sulfur compound is represented by the general formula (2) below:

Y—R—S—R'—Y     (2)

wherein
    Y independently represents hydroxyl, amino, isocyanate, aldehyde, carboxyl or its acid chloride, acid anhydride or acid amide, succinimidyl ester, succinimidyl carbonate, tresilyl, oxycarbonyl imidazole or nitrophenyl carbonate; and
    R and R' independently represent C$_2$–C$_{25}$ alkyl.

6. The material according to claim 5 wherein said sulfur compound of the formula (2) is one selected from the group consisting of thiodiethanol, thiodipropanol, methylthioethanol, methylthiopropanol, methylthiobutanol, ethylhydroxyethyl sulfide, glucose dimethylmercaptal, thioethyl ethylamine, thiodiglycolic acid, thiodipropionic acid, and methylthioacetic acid.

7. The material according to claim 1 wherein said sulfur compound is represented by the general formula (3) below:

Y—R—S—S—R'—Y     (3)

wherein
    Y independently represents hydroxyl, amino, isocyanate, aldehyde, carboxyl or its acid chloride, acid anhydride or acid amide, succinimidyl ester, succinimidyl carbonate, tresilyl, oxycarbonyl imidazole or nitrophenyl carbonate; and
    R and R' independently represent C$_2$–C$_{25}$ alkyl.

8. The material according to claim 7 wherein said sulfur compound of the formula (3) is one selected from the group consisting of hydroxyethyl disulfide, cystamine, dithiodipropionic acid, and dithiodibutyric acid.

9. The material according to claim 1 wherein said sulfur compound is represented by the general formula (4) below:

Y—R—O—CSSH     (4)

wherein
    Y is hydroxyl, amino, isocyanate, aldehyde, carboxyl or its acid chloride, acid anhydride or acid amide, succinimidyl ester, succinimidyl carbonate, tresilyl, oxycarbonyl imidazole or nitrophenyl carbonate; and
    R represents C$_2$–C$_{25}$ alkyl.

10. The material according to claim 1 wherein said sulfur compound is a compound represented by the general formula (5) below:

(Y—R)$_2$—N—CSSH     (5)

wherein
    Y is hydroxyl, amino, isocyanate, aldehyde, carboxyl or its acid chloride, acid anhydride or acid amide, succinimidyl ester, succinimidyl carbonate, tresilyl, oxycarbonyl imidazole or nitrophenyl carbonate; and R represents $C_2$–$C_{25}$ alkyl; or its salts or esters.

11. The material according to claim 1 wherein said metal substrate is one selected from the group consisting of stainless steel, titanium, nickel, chromium, copper, tantalum and an alloy thereof.

12. The material according to claim 1 wherein said thin film has a thickness of about 0.1 µm to about 100 µm.

13. A method for the production of a surface-modified medical metallic material, which comprises the steps of:
 (a) providing a metallic substrate;
 (b) coating a thin film of gold or silver on the surface of said substrate;
 (c) applying on said film a functional sulfur compound which can form a charge transfer complex with said film, thereby be adsorbed on said film; and
 (d) chemically bonding a sulfonated poly(ethylene oxide) (PEO) derivative to the functional groups of said sulfur compound.

14. The method according to claim 13 wherein the coating in step (b) is carried out by electroplating, thermal deposition, or ion sputtering method.

15. The method according to claim 13 which further comprises depositing an ultrathin film of chromium, titanium or an alloy thereof having a thickness of about 0.01 µm to about 1 µm on the surface of said substrate before step (b).

16. The method according to claim 13 wherein the chemical bonding in step (d) is carried out in the presence of esterification catalysts, amination catalysts, or substitution or addition reaction catalysts.

17. A stent comprising the surface-modified metallic material as defined in claim 1.

18. A cardiac valve comprising the surface-modified metallic material as defined in claim 1.

19. A catheter comprising the surface-modified metallic material as defined in claim 1.

* * * * *